United States Patent [19]

Wright et al.

[11] 4,304,552
[45] Dec. 8, 1981

[54] DENTAL WRENCH

[75] Inventors: David B. Wright, Wayne; Walter M. Bailey, Upper Darby, both of Pa.

[73] Assignee: Syntex (U.S.A.) Inc., Palo Alto, Calif.

[21] Appl. No.: 157,613

[22] Filed: Jun. 9, 1980

[51] Int. Cl.³ .............................................. A61C 1/08
[52] U.S. Cl. .................................... 433/126; 81/90 A
[58] Field of Search ............... 433/127, 126; 81/90 A; 279/1 K

[56] References Cited

U.S. PATENT DOCUMENTS 4,015,335 4/1977 Nash .................................... 433/127

Primary Examiner—Robert Peshock
Attorney, Agent, or Firm—John A. Dhuey; Joseph I. Hirsch

[57] ABSTRACT

A dental wrench is described having a structure which permits application of differing torques to the bur securing collet of a dental handpiece and the end cap of the turbine housing in a single wrench assembly. The wrench combines a shaft, for engaging the bur securing collet, supported rotatively in a frame member and secured to a support member which has means for engaging the end cap of the turbine housing. Interlocking means are provided between the support member and the frame member so that the wrench can be rotated as a unitary assembly to secure or remove the end cap of a turbine housing. The interlocking means are releaseable so that the shaft can be rotated independently within the frame member to secure or remove a dental bur in or from the collet of the handpiece housing. That portion of the frame member which is gripped for securing the end cap of the housing is of larger diameter relative to the support member so that increased torque can be applied to the end cap when the interlocking means is engaged to securely fasten the cap to the housing.

12 Claims, 6 Drawing Figures

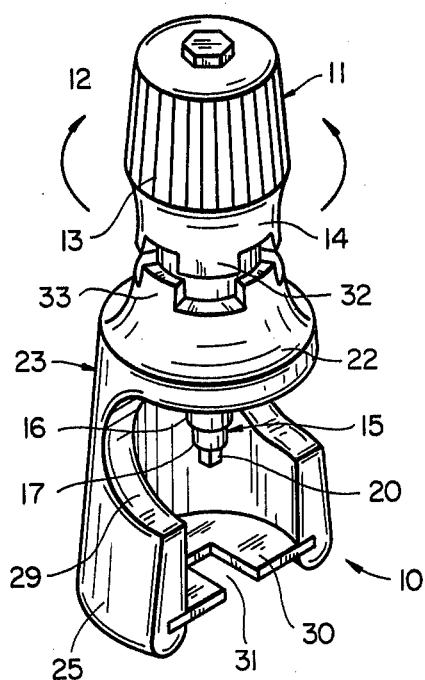
FIG_2
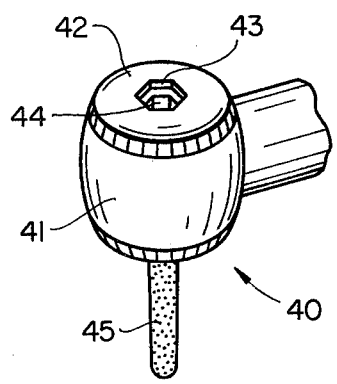
FIG_5
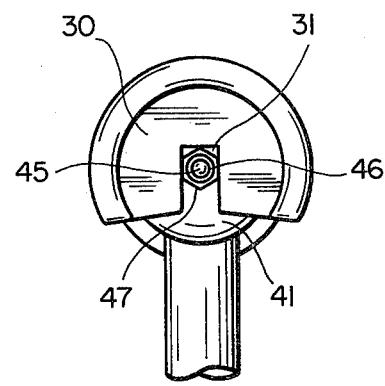
FIG_6

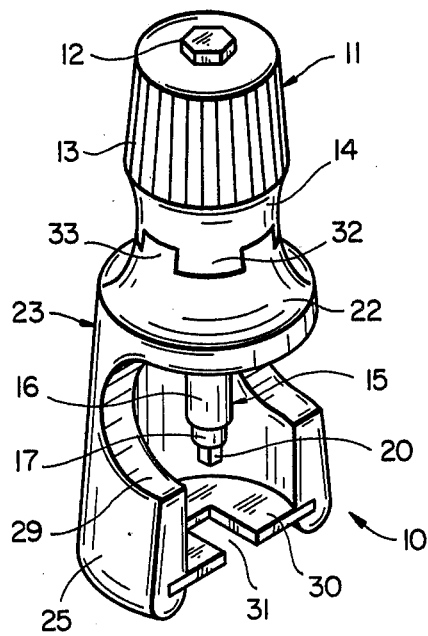
FIG_1
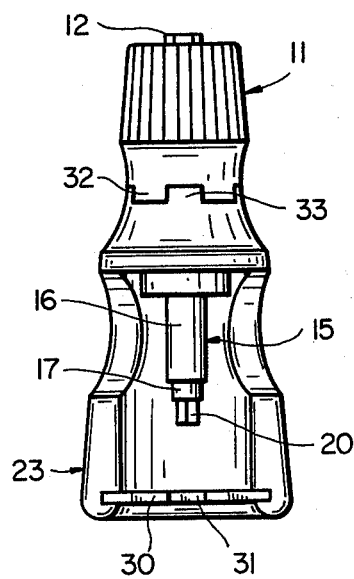
FIG_3
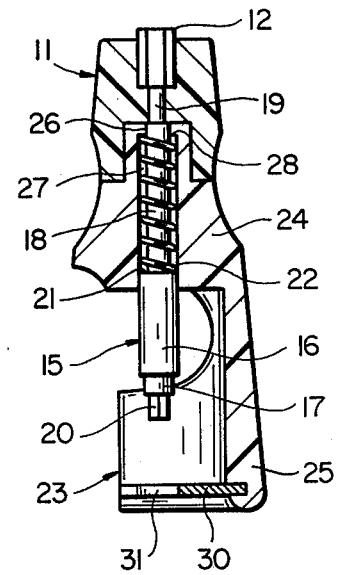
FIG_4

DENTAL WRENCH

BACKGROUND OF THE INVENTION

1. Field of the Invention

The present invention is concerned with a dental wrench. In particular, it is concerned with a bifunctional dental wrench which is utilized to engage and disengage a dental bur or other operative tool from the collet of a dental handpiece and to secure or remove a threaded end cap to the housing of a turbine cartridge assembly of the dental handpiece.

2. State of the Art

Various dental collet or chuck wrenches have been described in the art. Typically, such wrenches are mono-functional in that they are adapted to adjust a collet or chuck of a dental handpiece for engagement or disengagement with a dental bur or similar dental tool. Representative of the mono-functional dental wrenches are those described in U.S. Pat. Nos. 3,960,039; 3,888,008; 3,935,761; 3,947,966; and 4,033,040.

A dental wrench which utilizes a collet engaging tool and a turbine assembly housing end cap engaging tool is known in the art and is described in U.S. Patent Application Ser. No. 947,216, filed Sept. 29, 1978.

A problem associated with the prior art wrench has been the difficulty of applying sufficient torque to the end cap of the turbine housing on the dental handpiece such that the end cap does not loosen during operation of the handpiece. The small diameter rotatable knob on which is mounted the drive means to engage or disengage the end cap makes the application of sufficient torque to the end cap difficult since the resultant moment arm is small. It is generally not desirable to enlarge the diameter of the knob since the knob also is connected to the shaft which adjusts the collet or chuck mechanism for engaging or disengaging a dental bur or other tool. Application of excessive torque to the collet assembly can strip the threaded portions of the assembly and render it inoperative.

Accordingly, there is a need for a single dental wrench assembly which is bifunctional, so that it is possible to adjust the collet or chuck assemby of a handpiece and also engage or disengage the end cap on the turbine housing. It is also desirable to have a wrench which is constructed to permit application of greater torque when engaging the end cap with the housing of handpiece then when the collet assembly is being adjusted.

SUMMARY OF THE INVENTION

The wrench of the present invention comprises a frame member having a portion thereof adapted for gripping by an operator; a shaft slideably and rotatively received within the frame member; first engagement means on a first end of the shaft for engaging a first rotatable member; a support member secured to a second end of the shaft, the support member having a portion thereof adapted for gripping by an operator; second engagement means on the support member for engaging a second rotatable member; and interlocking means associated with the frame member and the support member, the grippable portion of the frame member and the grippable portion of the support member having different dimensions such that different torques can be applied through the first and second engagement means, and the interlocking means being operable in an engaged position wherein the frame member and the support member rotate as a unitary assembly but inoperable in a disengaged position wherein the support member rotates independently of the frame member.

In a preferred embodiment, the present invention comprises a dental wrench having a frame member, a shaft slideably and rotatively received within the frame member, first engagement means on a first end of the shaft for engaging a rotatable securing device, a support member secured to second end of the shaft, second engagement means on the support member for engaging a rotatable member and interlocking means associated with the frame member and the support member, the frame member having a grippable portion with a greater dimension than the dimension of a grippable portion of the support member, the interlocking means being operable in an engaged position wherein the frame member and the support member rotate as a unitary assembly but inoperable in a disengaged position wherein the support member rotates independently of the frame member.

DESCRIPTION OF THE DRAWINGS

FIG. 1 is a perspective view of the dental wrench with the interlocking means in the engaged position;

FIG. 2 is a perspective view of the dental wrench of FIG. 1 with the interlocking means in the disengaged position;

FIG. 3 is a front, elevational view of the dental wrench of FIG. 1;

FIG. 4 is a side, elevational view, in section, of the dental wrench of FIG. 1;

FIG. 5 is a perspective view of the housing of a typical dental handpiece with which the wrench of the present invention is utilized; and FIG. 6 is a bottom view of the dental wrench with the turbine housing in place in the wrench for operable engagement or disengagement of the collet assembly.

DETAILED DESCRIPTION OF THE INVENTION

With reference to the drawings, the dental wrench 10 of the present invention comprises a support member 11, a shaft 15 and a frame member 23. Support member 11 has a grippable portion 13, which can be knurled or ribbed to assist an operator in gripping support member 11, and a frame engaging portion 14. The top surface of support member 11 has an engaging means 12 thereon for engaging a rotatable member, such as the end cap of a turbine housing of a dental handpiece. A plurality of spaced lugs 32 are formed at the bottom of frame engaging portion 14, the function of which will be described hereinafter.

Secured to the lower end of support member 11 is a shaft 15. Shaft 15 is adapted to be slideably and rotatively received within upper portion 24 of frame member 23. Upper portion 24 is formed with a bore 26 and a counterbore 27. Bore 26 is of lesser diameter than counterbore 27 and their junction forms an internal shoulder 28 in frame member 23. Upper portion 24 has a plurality of spaced lugs 33 which cooperate with lugs 32 on support member 11 to provide the interlocking means of this invention.

Shaft 15 has a mid-portion 16 having a diameter slightly less than the diameter of counterbore 27 so that shaft 15 can rotate and slide upwardly and downwardly within counterbore 27 without binding. Extending from the lower end of midportion 16 is a boss 17 and engaging means 20 for engaging a rotatable securing device such as a collet or chuck mechanism in the turbine cartridge of a dental handpiece. Shoulder 21 on shaft 15 is formed at the junction of midportion 16 and the upper portion 18 of shaft 15. Shoulder 21 on shaft 15 and shoulder 28 on frame member 23 provide retention surfaces for biasing means such as spring 22. The upper end 19 of shaft 15 is secured to support member 11. The biasing action of spring 22 urges shaft 15 and support member 11 toward the lower end of frame member 23.

Frame member 23 is of generally frusto-conical shape with the diameter of the lower end of frame member 23 being larger than the diameter at its upper end and larger than the diameter of support member 11 which is of generally cylindrical shape. Lower portion 25 of frame member 23 is provided with cut-out portions 29 in the sidewalls of frame member 23 to create a space through which an operator can observe the positioning of the head of a dental handpiece when wrench 10 is placed about the head of the handpiece for engagement or disengagement of a bur or other dental tool from the collet or chuck of a turbine cartridge.

A locking plate 30 is secured at the lower end of lower portion 25 of frame member 23. Locking plate 30 has a slot 31 which is adapted to engage a cooperative member on the rotor shaft. Reference is made to U.S. Pat. No. 3,960,039, the disclosure of which is incorporated herein for reference, for a detailed description of the internal mechanisms and structure associated with typical turbine cartridge assemblies.

The dental wrench of this invention is particularly useful for turbine housings of dental handpieces as shown in FIG. 5. A representative handpiece 40 is illustrated with a turbine housing 41 having an end cap 42. End cap 42 is adapted to be threadably engaged with housing 41. A non-circular opening 43 is placed in end cap 42 to be engaged by a complementary tool for tightening or loosening of end cap 42 onto or from housing 41. Opening 43 is necessarily larger than non-circular opening 44 in the top of the threaded collet assembly so that opening 44 can be engaged by a complementary tool and rotated to engage or disengage the collet with or from a dental bur or similar tool when end cap 42 is secured to turbine housing 41.

In order to engage the collet of the dental handpiece 40, support member 11 is pulled upwardly to disengage lugs 32 and 33 as is shown most clearly in FIG. 2. In that configuration, spring 22 is compressed and urges shaft 15 downwardly toward the lower end of frame member 23. Housing 41 of handpiece 40 is inserted forwardly into the space defined by lower portion 25 of frame member 23. Cut-out portions 29 allow space for an operator to observe the positioning of housing 41 within wrench 10. Wrench 10 is positioned over housing 41 such that lock plate 30 and its slot 31 engage flat surfaces 47 on the rotor shaft of the turbine cartridge to prevent rotation of the rotor shaft when the collet is rotated, as shown in FIG. 6. Engagement means 20 of shaft 15 is non-circular about its perimeter and is adapted to engage complementary surfaces in opening 44 of the collet drive. Engagement means 20 of shaft 15 is inserted through opening 43 in end cap 42 and is rotated until the flat surfaces on engagement means 20 of shaft 15 engage the complementary surfaces in opening 44 of the collet drive. Spring 22 then urges shaft 15 downwardly such that engagement means 20 engages with opening 44 in the collet drive. Rotation of support member 11 imparts rotation to shaft 15, frame member 23 and dental handpiece 40 inserted therein being held stationary and the rotor shaft being held securely by slot 31 in locking plate 30. Interlocking lugs 32 and 33 are dimensioned such that support member 11 rotates independently of frame member 23 when engagement means 20 is engaged with opening 44 in the collet drive. With engagement means 20 engaged with opening 44 in the collet drive, shaft 15 and support member 11 secured thereto are maintained in a raised position such that the lower edges of lugs 32 on support member 11 are spaced from the upper edges of lugs 33 on frame member 23. Thus, support member 11 can be rotated while frame member 23 remains stationary.

After engagement or disengagement of a dental bur or similar tool from the turbine cartridge, support member 11 is pulled upwardly to disengage engagement means 20 of shaft 15 from opening 44 in housing 41 and housing 41 of handpiece 40 is removed from wrench 10.

Engagement means 12 on the top of support member 11 is adapted to engage opening 43 in end cap 42. Engagement means 12 and opening 43 are formed with non-circular perimeters and complementary surfaces such that rotation of engagement means 12 can impart torque through opening 43 to end cap 42. In order to apply sufficient torque to end cap 42 with wrench 10, support member 11 is interlocked with frame member 23 by means of cooperating lugs 32 and 33. Wrench 10 is inverted by an operator and gripped at the lower end of frame 23 near locking plate 30. The diameter of lower end 25 of frame 23 is substantially larger than the diameter of support member 11. Accordingly, greater torque can be applied to end cap 42 when using the wrench in the manner aforementioned than if an operator gripped support member 11 for rotation of engaging means 12.

The differing diameters of the members 11 and 23 in the structure of the present invention permit application of greater torque to end cap 42 than can be applied to the collet drive during rotation of shaft 15 by support member 11, with the use of a single, self-contained tool. It is thus not necessary for a dentist or other operator to keep two separate tools on hand. The bifunctional wrench of this invention in a single structure is adapted to independently engage the collet drive mechanism and the end cap on the housing of a handpiece assembly.

The invention has been illustrated in the situation wherein it is desirable to apply greater torque to the end cap of the housing of a handpiece assembly than to the collet drive mechanism of the handpiece. In other applications, it might be desirable to apply greater torque through engagement means 20 than through engagement means 12. In those instances, the wrench can be modified such that the dimension of a grippable portion of support member 11 is greater than the dimension of a grippable portion of frame member 23. In that embodiment, the moment arm operating on engagement means 20 will be greater than the moment arm operating on engagement means 12, and consequently the torque applied through engagement means 20 will be greater than the torque applied through engagement means 12. The interlocking means as hereinbefore described permits independent application of the differing torques as required.

Although this invention has been described with reference to the specific embodiments illustrated in the drawings, it should be understood that those skilled in the art will perceive various modifications and equivalent structures which may be substituted for those illustrated herein without departing from the true spirit and scope of the invention. All such modifications and equivalents are intended to be within the scope of the claims appended hereto.

What is claimed is:

1. A dental wrench comprising:
a frame member;
a shaft slideably and rotatively received within said frame member;
first engagement means on a first end of said shaft for engaging a rotatable securing device;
a support member secured to a second end of said shaft;
second engagement means on said support member for engaging a rotatable member; and
interlocking means associated with said frame member and said support member,
said frame member having a grippable portion of greater dimension than the dimension of a grippable portion of said support member, and said interlocking means being operable in an engaged position wherein said frame member and said support member rotate as a unitary assembly but inoperable in a disengaged position wherein said support member rotates independently of said frame member.

2. A dental wrench of claim 1 wherein said interlocking means comprises a set of spaced, cooperative lugs on said support member and a set of spaced, cooperative lugs on said frame member, said lugs on one member being adapted to engage the corresponding lugs on the other member for rotation of the wrench as a unitary assembly.

3. A dental wrench of claim 1 wherein said shaft is biased toward the lower end of said frame member.

4. A dental wrench of claims 1, 2 or 3 wherein said frame member includes means at its lower end for preventing rotation of a rotor shaft of a dental handpiece.

5. A dental wrench of claim 4 wherein said means for preventing rotation of a rotor shaft comprises a locking plate on said frame member having a non-circular slot therein, said slot being adapted to engage a complementary non-circular portion of the rotor shaft.

6. A dental wrench comprising:
a frame member having a generally frusto-conical shape, said frame member defining an opening for receiving the housing of a turbine assembly of a dental handpiece and having a vertical bore in the upper end thereof coaxial with the central axis of said frame member;
a shaft slideably and rotatively received within the bore of said frame member, said shaft having an upper end and a lower end,
first engagement means on the lower end of said shaft for engaging a rotatable securing device;
a generally cylindrical support member secured to the upper end of said shaft, said cylindrical support member having a diameter less than the largest diameter of said frame member;
second engagement means on the upper end of said cylindrical support member for engaging a rotatable member; and
interlocking means associated with said frame member and said support member for rotating said wrench as a unitary assembly, said interlocking means being operable in an engaged position wherein said frame member and said support member rotate as a unitary assembly but inoperable in a disengaged position wherein and said support member rotates independently of said frame member.

7. A dental wrench of claim 6 wherein said interlocking means comprises a set of spaced, cooperative lugs on said support member and a set of spaced, cooperative lugs on said frame member, said lugs on one member being adapted to engage the corresponding lugs on the other member for rotation of the wrench as a unitary assembly.

8. A dental wrench of claim 6 wherein said shaft is biased toward the lower end of said frame member.

9. A dental wrench of claims 6, 7 or 8 wherein said frame member includes means at its lower end for preventing rotation of a rotor shaft of a dental handpiece.

10. A dental wrench of claim 9 wherein said means for preventing rotation of a rotor shaft comprises a locking plate on said frame member having a non-circular slot therein, said slot being adapted to engage a complementary non-circular portion of the rotor shaft.

11. A wrench comprising:
a frame member having a portion thereof adapted for gripping by an operator;
a shaft slideably and rotatively received within said frame member;
first engagement means on a first end of said shaft for engaging a first rotatable member;
a support member secured to a second end of said shaft, said support member having a portion thereof adapted for gripping by an operator;
second engagement means on said support member for engaging a second rotatable member; and
interlocking means associated with said frame member and said support member,
the grippable portion of said frame member and the grippable portion of said support member having different dimensions such that different torques can be applied through said first and second engagement means, and said interlocking means being operable in an engaged position wherein said frame member and said support member rotate as a unitary assembly but inoperable in a disengaged position wherein said support member rotates independently of said frame member.

12. A wrench of claim 11 wherein said interlocking means comprises a set of spaced, cooperative lugs on said support member and a set of spaced, cooperative lugs on said frame member, said lugs on one member being adapted to engage the corresponding lugs on the other member for rotation of the wrench as a unitary assembly.

* * * * *